United States Patent [19]

Holbrook

[11] E Re. 29,321

[45] Reissued July 26, 1977

[54] FLUID COLLECTION BOTTLE AND IMPROVEMENTS THEREIN

[75] Inventor: LeGrand K. Holbrook, Salt Lake City, Utah

[73] Assignee: Medical Development Corporation, Salt Lake City, Utah

[21] Appl. No.: 640,059

[22] Filed: Dec. 12, 1975

Related U.S. Patent Documents

Reissue of:

[64] Patent No.: 3,878,962
Issued: Apr. 22, 1975
Appl. No.: 412,329
Filed: Nov. 2, 1973

U.S. Applications:

[63] Continuation of Ser. No. 857,161, Sept. 11, 1969, abandoned.

[51] Int. Cl.[2] ..... B65D 47/12
[52] U.S. Cl. ..... 215/309; 128/276
[58] Field of Search ..... 215/307, 308, 309, 311; 128/272, 275, 276, 277, 278, 300, 301

[56] References Cited

U.S. PATENT DOCUMENTS

| | | | |
|---|---|---|---|
| 489,786 | 1/1893 | Bonbrake | 220/66 X |
| 948,115 | 2/1910 | McCourtie | 128/278 X |
| 1,056,241 | 3/1913 | Wennersten | 215/309 X |
| 2,024,532 | 12/1935 | Mancuso | 215/262 |
| 2,982,440 | 5/1961 | Harrison | 220/66 |
| 3,032,037 | 5/1962 | Huber | 128/276 |
| 3,429,313 | 2/1969 | Romanelli | 128/276 |
| 3,620,408 | 11/1971 | Holbrook | 215/1 C UX |

*Primary Examiner*—Donald F. Norton
*Attorney, Agent, or Firm*—Fitch, Even, Tabin & Luedeka

[57] ABSTRACT

The present invention comprises a vacuum-operated, fluid-collection bottle having advantageous, canted sealing surfaces between cover and container as well as other improvements including a perforate vacuum fitting, spherical top and bottom, [both convex and concave; float valve means incorporated in the vacuum port construction;] snap-lock engagement between the cover and container; graduation means for measuring small volumes of collected fluid, and so forth.

6 Claims, 2 Drawing Figures

FLUID COLLECTION BOTTLE AND IMPROVEMENTS THEREIN

Matter enclosed in heavy brackets [ ] appears in the original patent but forms no part of this reissue specification; matter printed in italics indicates the additions made by reissue.

This is a continuation of U.S. patent application Ser. No. 857,161, filed Sept. 11, 1969, by the same title now abandoned.

The present invention relates to vacuum operated, fluid collection bottles and, more particularly, to a new and improved bottle of the type described which can be used for collecting the body fluids of patients in hospital operating rooms, recovery rooms, and so forth, by way of example.

In the past, a limited number of fluid collection bottles designed for vacuum operation have been devised. These bottles are separable, in that the bottle includes a container and a cover. Prior designs of which the inventors are aware, indicate that the covers and bottoms of such bottles are generally flat and made of glass. Disposable-type bottles, those which the inventors presently contemplate, are to be made of a suitable plastic that requires special design considerations. For vacuum operation, plastics suitable for disposable units are somewhat flexible. Hence, deformation of the general contour of the bottle will occur upon the application of suitable reduced-pressure, for drawing fluid into the bottle. It is desirous, of course, to reduce such deformation to a minimum in order to preserve the integrity of the bottle, its volume, and the seal thereof between the cover and container.

[Accordingly, a principal object of the present invention is to provide a fluid collection bottle.]

An [additional] object is to provide a new and improved body fluid collection bottle for hospital use.

A further object is to provide a fluid collection bottle having [either convex or] concave top and bottom surfaces.

An additional object is to provide a uniquely [configures] *configured* cover construction in a fluid collection bottle which will not distort, at least appreciably, when a reduced pressure is applied to the interior of the bottle.

An additional object is to provide a vacuum bottle such as that having [a dome shaped cover,] a vacuum port inlet [in conjunction with a unique float valve shut-off].

An additional object is to provide a container-cover construction for a vacuum bottle wherein the adjacent sealing surfaces thereof are configured to provide a maximum sealing effect.

A further object is to provide a vacuum bottle construction wherein a flexible cover thereof is simply snapped onto the container of the construction.

In accordance with the present invention, the over-all vacuum bottle construction includes a cover and bottom which [in one form of the invention are dome shaped and in the other form of the invention] are concave outwardly. [These constructions rely] *This construction relies* on the compression or tensile strength of the material to preserve the integrity of the configuration of the bottle design when vacuum pressure is applied. [In one form of the invention, a float-operated, shut-off valve is provided the vacuum port operatively associated with the cover of the bottle.] Unique surface-seal means is provided such that any slight deformation of the cover of the bottle is utilized to provide an adequate seal proximately *of the* top rim of the container bottle when vacuum is applied. An annular, ring-like protuberance and groove intercooperate to lock the cover of the bottle to the container thereof. Graduation markings are supplied [at the bottom of the container] so that [small] amounts of fluid may be measured in the [spherical bottom of the] container.

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

FIG. 3 is an enlarged fragmentary section, taken along the line 3—3 in FIG. 1.]

FIG. [4] *2* is an enlarged fragmentary section along the line [4—4] *2—2* in FIG. [2.] *1*.

Figure 1:
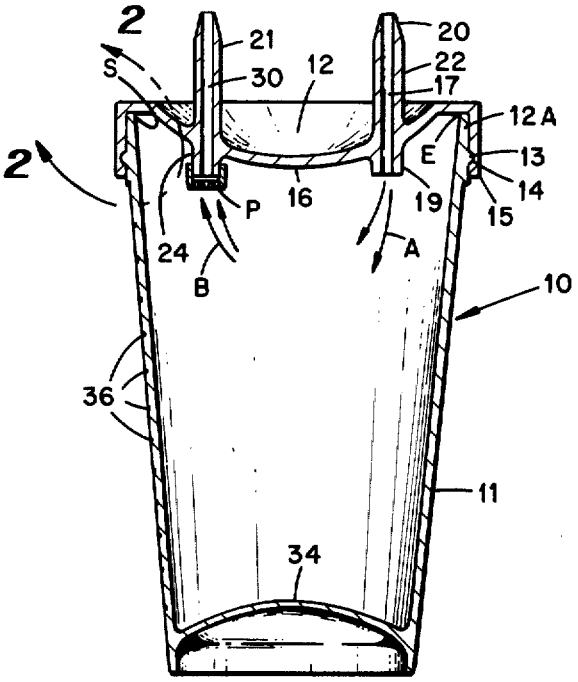
FIG. 1 is an elevation in section, taken along a vertical, transverse medial plane, of a fluid collection bottle incorporating the features of the present invention.

In FIG. 1, fluid bottle 10 is shown to include a container 11 and also a cover 12. Container 11 includes an upper protruding margin [12] *12A* provided with an annular bead 13. Bead 13 is designed to fit as a sealing detent into annular recess 14 of the depending lip 15 of cover 12. Cover 12 also includes a [top, dome, or] rigid end wall provided with fluid aperture 17 and vacuum aperture 30. These apertures are respectively delineated by depending tubular portions 19 and 24. These may be integrally formed with cover 12, if desired.

Cover 12 also includes ports 21 and 22 for receiving the end fittings or end portions of conventional vacuum and fluid, tubes or hoses, not shown. The end of ports 21 and 22 are preferably tapered as shown at [22,] *20* so as to provide for the wedging of *an* end fitting [23] thereupon.

[Port 21 is provided with a depending tube 24 having a cylindrical float chamber 25. Slidably but tightly disposed within chamber 25 is a valve gate 26. Stem 27 is secured to valve gate 26, is rigid in nature, and includes at its lower end a ball float 28. Apertures 29 and 18 are provided in the construction, as seen in FIG. 3. A C-ring retainer 31 may be provided to co-operate with annular internal grooves 32, and the C-ring retainer serves as a limit stop abutment for float 28 to preclude the latter from dropping into the interior of the container.

Where a vacuum shut-off is needed relative to the interior of container 11, then the structure as seen in enlarged view in FIG. 3 is appropriate. Thus, as the fluid level within container 11 rises, the same will ultimately contact float 28, causing the same to rise; by virtue of the rigid stem 27, the valve gate 26 will rise also. Forward surface 26A will ultimately close off aperture 30 such that the suction applied to the interior of the bottle is substantially reduced if not eliminated. As a safety feature, should the fluid level continue to rise, then the rear surface 26B of the valve gate 26 will close off port 29, thereby providing as a safety feature a double shut-off relative to the apertures 29 and 30. Seat 33 may be configured to match exactly the contour at 26C, the top of the valve gate 26.]

In returning to a consideration of container 11, it is seen that the bottom thereof is concave upwardly. The bottom is designated as 34. [and the same may include annular interior markings or graduations 35. Further markings] *Markings* may [, of course,] be present at several incremental levels 36. These markings may be engraved, grooved, or otherwise applied to the container. Preferably, container 11 will be transparent so that the observer can easily note [not only] those markings exterior of the bottle. [but also the interior markings 35 as well. Interior markings 35 are ideally used where very small amounts of blood need to be accurately measured. This is especially important in operative situations involving infants.]

*The top portion 16 of the cover 12 is convex downwardly and the bottom end wall 34 of the container is convex upwardly. Such a construction serves very well in connection with the vacuum techniques since, when vacuum is applied, the inherent strength of the materials of container 11 and cover 12 permits the tensioning of the bottom and top without essential distortion.*

The ["dome"] nature of top 16 of cover 12, and the bottom 34 of the container 11, serve the important purpose of pre-stressing the structure, when vacuum is applied to the container. Thus, it is anticipated that a minimum of distortion of container 11 in cover 12 will occur when vacuum is applied. Additionally, a desired edge seal is produced as between the upper edge E of the container and the corresponding surface S on the underneath side of cover 12. In cases where bottom end wall 34 of container 11 and the top portion 16 of cover 12 are simply horizontal and planarly configured, then the application of vacuum to port 21 tends to displace these two surfaces inwardly. This action tends to distort slightly the over-all configuration of the bottle and may in some instances have a deleterious effect on the vacuum seal between the container and cover. Where the [dome] construction relative to cover 12 is utilised as in FIG. 1, then such displacement is less likely to occur and the seal and contour of depending lip 15 tend to be preserved. [In addition, where circular graduations 35 are used at spherically concave bottom end wall 34, then appropriate determination of small volumes of fluid which accumulate at the bottom of the container can be accurately measured.] Bottom 34 also compliments the action and effectiveness of configuration of cover 12 so that greater strength of the over-all bottom construction is ensured. Additionally, the configuration of rigid bottom end wall 34 is less likely to become deformed when vacuum is applied.

In the operation, the tube or hose, not shown, connected to [end fitting 23] *port 22* is routed to the general operative area of the patient and a vacuum hose connected to port 21. When vacuum is thus applied, the body fluid of the patient will be conducted by its hose through [end fitting 23 and] port 22 into the interior of the container 11 as indicated by arrows A. This again, is by virtue of evacuation of the interior of the bottle as shown by arrows B. The body fluid of the patient is easily measured [, first, as to small amounts, by the bottom graduations 35 and, as the fluid continues to rise,] by the outermost, spaced graduations 36.

[When the fluid level reaches float 28, in FIG. 3, the valve gate 26 of valve construction V rises to close, first, aperture 30 and, second, aperture 29. Such a closure of valve V operates to terminate the suction within the fluid bottle 10 so that the further drawing of fluid into the bottle is precluded. A new bottle is thus installed, the old one removed, and the draining process is continued.

Figure 2:
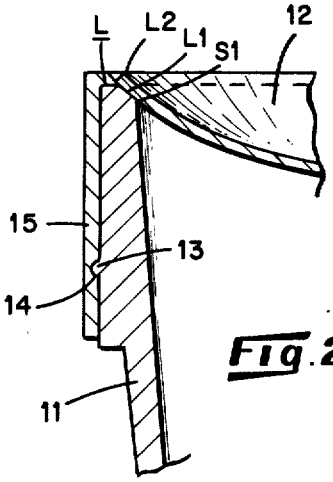
[FIG. 2 is a view similar to FIG. 1, but illustrates an alternate form of bottle construction.

FIG. 2 illustrates a slightly modified construction of the invention wherein ports 21A and 22A are slightly differently configured as illustrated.] A perforate cap P is fitted over the vacuum port to prevent foam and blood from being drawn up this port to the vacuum pump. The porting construction in FIG. [2] *1* indicates that both ports, if desired, may be vertically oriented. [As seen in FIG. 2, the bottom end wall 35A of the container is this time convex upwardly, with top portion or end wall 16A being convex downwardly. Such a construction serves very well in connection with the vacuum techniques since, when vacuum is applied, the inherent strength of the materials of container 11A and cover 12A permits the tensioning of bottom and top without essential distortion.] In practice, it will be found that [either the outwardly-convex configuration of FIG. 1 or] the outwardly-concave configuration of FIG. [2] *1* will serve very well in connection with the vacuum techniques employed with fluid bottles. The particular construction selected will depend upon the character of the plastics or other materials used and their abilities to withstand both stress and strain by the vacuum pressures contemplated, and so forth. What is important, in a preferred form of the invention, is that the top and bottom of the bottle construction be not horizontally planar, but rather arcuate as shown *in FIG. 1* so that the vacuum seal between the cover and container as well as the inter-engagement thereof may be preserved.

FIG. [4] *2* illustrates in enlarged, fragmentary section that a preferred form of the upper lip L of container 11 includes a canted portion L1 as well as a straight or horizontal portion L2. The portion L2 serves to support the sealing surface on cover [12A] *12*. But with such support, experimentation has indicated that there is needed an effective, canted, beveled, or slightly chamfered sealing surface S1. The same may be used to draw down and thus seat any transversely flexible cover used with container 11. Such a sealing surface may exactly fit the contour of a cover such as cover [12A] *12* in FIG. 2, or the same may be even employed with any other type of cover designs wherein the cover itself is sufficiently flexible so as to permit such a "drawing down" in the seating of the cover at seal area S1 in FIG. [4.] *2.* The materials suggested with regard to such inherent flexibility relative to cover 12, are polystyrene, polyethylene, polyurethane. The same materials, howbeit of stiffer grade, may be conventionally employed for container 11. Cover 12, of course, should have sufficient flexibility such that the depending rim 15 of the cover may be passed over and snapped into engagement with the annular bead 13 of container 11.

What is provided is a new and improved body fluid bottle construction which is easily assembled and installed for use. [The same may include the float valve if desired, as shown in FIG. 1.] Of importance is that adequate sealing surface means are provided as between the container and cover so that an effective vacuum seal may be preserved during operation of the equipment. Further, distortion during use of the bottle is substantially reduced if not eliminated by the inclusion of curved bottom and top surfaces of the bottle construction. These will generally comprise spherical sections as shown such that the [dome] *cover* and bottom of the overall bottle construction [may] *will* be [either convex outwardly or] concave outwardly. Specifically, the concave cover design of FIG. [2] *1* prevents noticeable distortion of the cover upon the application of vacuum pressure, and this is paramount to the total design of this preferred embodiment of the system.

Again, the selection of the specific design will depend upon usage, the materials desired in construction of the bottle, and so forth.

While particular embodiments of the present invention have been shown and described, it will be obvious to those skilled in the art that changes and modifications may be made without departing from this invention in its broader aspects.

We claim:

1. A vacuum operated fluid collection bottle for recovering body fluids and comprising a container and a centrally concave cover *removably* secured thereto, said concave cover being essentially rigid and having an inwardly convex interior surface and an outwardly concave exterior surface, said concave cover being essentially rigidly constructed in such configuration, prior to vacuum application, whereby to insure against cover collapse when a vacuum is applied, said [bottle] *cover* being provided with a fluid admittance port and a vacuum port, both of said ports communicating with the interior of said bottle.

2. The structure of claim 1 wherein said container includes an upper annular lip, said cover includes [am] *an* annular flange overlapping and sealingly engaging said lip.

3. A vacuum-operated fluid collection bottle including, in combination, a container having an upper lip, and a cover sealingly *and removably* secured to said container, said cover having plural, exteriorly connectable, bottle interior communication ports, said cover including a concave central portion and an annular portion integral with said central portion and encompassing said container lip, said central portion having a concave surface facing outwardly and a convex surface facing inwardly *said cover being so constructed, prior to vacuum application.*

4. A vacuum-operated body fluid collection bottle having cross-sectionally arcuate, inwardly concave, essentially rigid opposite, concavo-convex end walls, constructed so prior to vacuum application, one of said end walls being provided with a fluid admittance port and a vacuum port, both of said ports communicating with the interior of said bottle, one of said end walls comprising a cover having a depending annular flange encompassing said bottle.

5. In a vacuum operated fluid collection bottle comprising the combination of a container and an independent cover releasably secured over said container, said container and said cover having inter-cooperating means whereby said container and cover can be releasably retained together in a sealing engagement, said combination being provided with fluid inlet port means and vacuum port means mutually spaced apart; and improvements wherein said cover has an essentially rigid concave construction, prior to and after vacuum application, protruding in a direction toward the interior of said container, whereby, when a vacuum is applied via said vacuum port means, said concave construction will preserve bottle integrity against container and cover collapse, said cover thereby having an inwardly convex interior surface and a concave outer surface facing outwardly.

6. The structure of claim 5 wherein said cover is provided with said fluid inlet port means and said vacuum port means.

* * * * *